United States Patent [19]  
Nowinski et al.

[11] Patent Number: 4,752,638  
[45] Date of Patent: * Jun. 21, 1988

[54] SYNTHESIS AND USE OF POLYMERS CONTAINING INTEGRAL BINDING-PAIR MEMBERS

[75] Inventors: Robert C. Nowinski; Allan S. Hoffman, both of Seattle; Raymond L. Houghton, Kirkland; John H. Priest, Everett; Nobuo Monji, Seattle, all of Wash.

[73] Assignee: Genetic Systems Corporation, Seattle, Wash.

[*] Notice: The portion of the term of this patent subsequent to Apr. 16, 2002 has been disclaimed.

[21] Appl. No.: 880,122

[22] Filed: Jun. 30, 1986

Related U.S. Application Data

[63] Continuation-in-part of Ser. No. 668,248, Nov. 7, 1984, Pat. No. 4,609,707, which is a continuation-in-part of Ser. No. 600,383, Apr. 16, 1984, abandoned, which is a continuation-in-part of Ser. No. 550,929, Nov. 10, 1983, Pat. No. 4,511,478.

[51] Int. Cl.$^4$ .......................... C08L 89/00; C08H 1/00  
[52] U.S. Cl. .................................. 525/54.1; 526/238.1; 436/531; 436/535; 436/541; 436/543; 436/827; 210/692; 530/405; 530/817

[58] Field of Search .................. 525/54.1, 54.11; 526/238.11; 436/531, 535, 541, 543, 827; 210/692; 530/405, 817

[56] References Cited

U.S. PATENT DOCUMENTS

| | | | |
|---|---|---|---|
| 2,853,457 | 9/1958 | Gates, Jr. et al. | 526/238.1 |
| 3,969,287 | 7/1976 | Jaworek et al. | 526/238.1 |
| 4,061,466 | 12/1977 | Sjohölm et al. | 436/535 |
| 4,195,129 | 3/1980 | Fukui et al. | 435/182 |

Primary Examiner—John Kight  
Assistant Examiner—Nathan M. Nutter  
Attorney, Agent, or Firm—Bertram I. Rowland

[57] ABSTRACT

Conjugate monomers, polymers, and methods for the de novo synthesis of the polymers are provided. Conjugate organic monomers contain binding-pair members which upon polymerization become integrally associated with the resultant polymer. Specifically, antigens, antibodies, receptors, and ligands may be bound to organic monomers either directly by chemical reaction or indirectly by chemical spacer arms, and these conjugates may be polymerized or copolymerized with non-derivatized monomers to form polymers containing variable amounts of the binding-pair members. Such conjugate monomers and polymers find a wide variety of uses in binding to their binding-pair-member cognate which include selective removal of complementary binding-pair members from solution as well as in immunoassay procedures and in immunization regimes.

31 Claims, No Drawings

SYNTHESIS AND USE OF POLYMERS CONTAINING INTEGRAL BINDING-PAIR MEMBERS

BACKGROUND OF THE INVENTION

1. Field of the Invention

It is frequently desirable to be able to bind, detect, or remove a particular compound in a medium suspected or known to contain that compound. The present invention relates to conjugate monomers containing binding-pair members, to polymers synthesized from these conjugate monomers and to the de novo synthesis of these polymers. The polymers contain the binding-pair members as integral parts of their structure and find use in selective removal of binding-pair-member cognates from solution as well as in various immunoassay procedures and immunization regimes.

2. Description of the Relevant Art

Polymerization of monomers or oligomers to form larger polymeric molecular structures (polymers) or the initiation of copolymerization of monomers with polymerizable polyunsaturated compounds is fundamental to polymer chemistry. Polymers may be formed from a single monomeric species (homopolymers), from a mixture of different monomers (copolymers), from polymerizable polyunsaturated compounds containing olefinic or acetylenic unsaturation, or from a mixture of polymerizable polyunsaturated compounds and one or more monomers. Linear, branched or cross-linked polymeric structures are possible.

By varying the chemical composition and/or ratios of the monomer and/or polyunsaturated compound, it is possible to form either water-soluble or water-insoluble polymers which have a broad range of chemical and physical properties. For example, water-soluble monomers (such as acrylamide) may be homopolymerized to form water-soluble homopolymers. Such monomers may also be copolymerized with less water-soluble monomers (such as N-alkyl or N,N-dialkyl acrylamide) or with cross-linking monomers (such as N,N'-methylenebisacrylamide) to form water-insoluble copolymers. Some water-soluble monomers (such as 2-hydroxyethylmethacrylate or acrylonitrile) may be homopolymerized to form water-insoluble homopolymers.

Water-insoluble polymers (such as polysaccharides and polyacrylics) have been commonly used in the fields of biochemistry and immunology (affinity chromatography and immunoassay) as solid phase supports with passively adsorbed or covalently linked antibodies. To date, however, antibodies have only been immobilized on preformed insoluble polymeric materials. For example, antibodies can be covalently bonded to cyanogen bromide-activated beads of Sepharose-4B or beads of cross-linked acrylic polymers (U.S. Pat. No. 3,957,741). Also, see *Affinity Chromatography and Related Techniques*, Proceedings of the Fourth International Symposium, Veldhove, The Netherlands, June 22-26, 1981, Ed. P. C. J. Gribnau, J. Visser and R. C. S. Nivard, Elsevier Scientific Publishing Company, New York, 1982. The immobilized antibodies can then be used to specifically bind antigens to the solid surface of the beads followed by extensive washing to remove other adsorbed substances. Subsequently the bound antigens can be eluted from the antibody/polymer mat by treatment with chaotropic agents, high salt concentrations or low pH buffers. Antibodies have also been confined within encapsulated membranes for use in affinity chromatography (U.S. Pat. No. 4,257,884).

U.S. Pat. Nos. 3,314,905 and 3,453,222 disclose reaction products of proteinaceous materials and certain esters to form substances which are capable of polymerization (modified proteins). The reaction conditions under which these modified proteins are synthesized are harsh, e.g., elevated temperatures (typically 50° C.) and high pH (typically >8). The end products have use as resin-protein wood adhesives or flocculating agents.

U.S. Pat. No. 2,548,520 discloses high molecular weight materials prepared by copolymerizing proteins having unsaturated radicals chemically united therewith with unsaturated polymerizable monomers or their partial polymerization products. Production of these high molecular weight materials generally requires temperatures up to 100° C. Such high temperatures are not well tolerated by most proteins. Thus methods as described are unsuitable for producing polymers of biologically active molecules.

U.S. Pat. No. 3,969,287 discloses a method for the preparation of carrier-bound proteins wherein the protein is reacted with a coupling compound containing at least one double bond capable of copolymerization. The carrier is provided as a water-insoluble solid or is produced in situ by the polymerization of water-soluble monomers in the presence of the protein/coupling compound adduct. The proteins utilized in the methods of this invention are typically enzymes, and, of those disclosed, none contain multiple subunits.

In immunoassays (see Campbell, D. H. and Weliky, N. *Methods in Immunology and Immunochemistry*, Ed. Williams and Chase, Vol. I, Academic Press, New York, 1967), antibodies or antigens have been passively adsorbed to surfaces, e.g., to the wells of microtiter plates, plastic beads (U.S. Pat. No. 4,225,784), or latex particles. The solid phase antibody/polymer matrix provides a selective binding surface which, following antigen binding, can be washed to separate bound from unbound reactants. Also known is (a) the covalent bonding of antigens or antibodies to latex beads (U.S. Pat. No. 4,181,636) or high-refractive-index particles (U.S. Pat. No. 4,401,765) to measure agglutination reactions or (b) the binding of antibodies to fluorescent polymer beads to provide specific tags for cell-surface antigens (U.S. Pat. No. 4,166,105).

While the insoluble polymer/antibody materials described above provide a surface upon which selective biochemical or immunological reactions can occur, the polymers formed by bonding a molecule to an already formed polymeric material are limited in that the spacing, steric accessibility, and number of antibody molecules bound per unit length of polymer cannot be precisely or reproducibly controlled. Lot-to-lot variation is commonly encountered during the manufacture of such solid phase polymers. In certain end-use applications where reproducibility and standardization are important (e.g., immunoassays), the variation in composition of the solid phase polymer/antibody material may not be acceptable.

SUMMARY OF THE INVENTION

Polymers and methods for the de novo synthesis of these polymers are provided wherein the polymes integrally contain binding-pair members. Conjugate organic monomers are synthesized that contain binging-pair members which are bound either directly or indirectly via chemical spacer arms. These conjugate monomers may be polymerized or copolymerized with non-derivatized monomers to produce polymers in which the number of integral binding-pair members may be determined by variations in polymerization conditions and reaction stoichiometry. Binding-paper members include receptors, e.g., antibodies and ligands, e.g., antigens, and the like. The resulting polymers can find use in selective removal of binding-pair-member cognates from solution as well as in immunization regimes and in various immunoassay procedures.

DESCRIPTION OF THE SPECIFIC EMBODIMENTS

Monomer conjugates containing specific binding-pair members, polymers of such monomer conjugates, and the de novo preparation of such polymers are provided. The subject monomer conjugates and polymers integrally containing in their structure binding-air members find use in selective removal of binding-pair-member cognates from solution, in immunoassays, and in immunization regimes. Other uses will become apparent from the following description and associated claims.

Initially the monomer/binding-pair-member conjugate is synthesized, which is then followed by polymerization of the conjugate with itself or copolymerization of the conjugate with a predetermined amount of non-derivatized polymerizable unsaturated compounds to form polymers integrally containing the binding-pair members. Binding-pair members are chemical species that have a preferential binding affinity for one another which include, but are not limited to, antibody-antigen, receptor-ligand (e.g., in addition to antibody receptors, hormone receptors, drug receptors, lectins, transport proteins, antibody binding proteins, etc.) and their cognate ligands and the like. Receptors may be naturally-occurring, the result of deliberate immunization, synthesized chemically, or synthesized by using recombinant DNA and include antibodies which are monoclonal or polyclonal.

The monomer/binding-pair-member conjugates are produced by conjugating one or more appropriate monomers with one or more specific binding-pair members. This linkage may be direct or the binding-pair member may be indirectly conjugated to the monomer via an intermediate chemical compound functioning as a spacer arm to physically separate the monomer from the binding pair members. For specific binding-pair members of less than about 1000 molecular weight, usually the ratio of derivatizable monomers to specific binding-pair members is less than about 10:1, more usually less than about 5:1 and normally greater than about 0.02:1, more normally greater than about 0.1:1, and preferably greater than about 0.5:1. For specific binding-pair members greater than about 1000 molecular weight, usually the ratios of derivatizable monomers to specific binding-pair members is less than about 50:1 and more usually less than about 25:1 and normally greater than about 0.5:1.

For purposes of the present invention, the term "monomer" means any addition-polymerizable organic compound which is capable of forming covalent linkages (i.e., polymerization) under the appropriate conditions and includes certain polyunsaturated monomers or oligomers. The term "nonderivatized polymerizable unsaturated compound" means those organic compounds capable of being polymerized under appropriate conditions that are not conjugated to a binding-pair member. The term "integrally containing" means that the binding-pair member is conjugated to a component of the polymer directly or indirectly, prior to or as the polymer is being formed, rather than being conjugated to a preformed polymer.

Monomers which can be used include those having ethylenic or acetylenic unsaturation and at least one reactive site for conjugation to a corresponding reactive site on the binding pair members or to an intermediate chemical compound functioning as a spacer arm. Such monomers may include: (a) molecules containing olefinic unsaturated groups and at least one reactive site for conjugation to the binding-pair member or spacer-arm compound, e.g., vinyl, allyl, or vinylene monomers; (b) molecules having acetylenic unsaturation and at least one reactive site for conjugation to the binding-pair member or spacer arm group; and (c) polyunsaturated molecules, such as monomers containing olefinic unsaturation and having at least one aliphatically unsaturated reactive site for conjugation to the binding pair member or spacer arm compound, e.g., diene.

Monomers which may be used include the following:

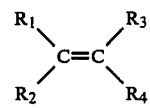

where $R_1$ and $R_3$ equal H or methyl; $R_2$ equals H, methyl, or ethylene; and $R_4$ equals;

—COCl
—CN
—OH
—COOH
—COOR$_5$ where R$_5$=an alkyl group having from 1-6 carbon atoms;

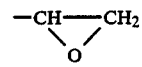

—CO$_2$(C$_n$H$_{2n}$)OH where n=2 to 4
—NH$_2$
—NHR$_5$ where R$_5$ is defined as above;
—NCO
—CONH$_2$
—CONHR$_5$ where R$_5$ is defined as above;
—CONHCH$_2$OH
—CH$_2$NH$_2$
—CH$_2$Cl
—CO$_2$(C$_n$H$_{2n}$)NH$_2$ where n is defined as above;
—CO$_2$(C$_n$H$_{2n}$)NHR$_5$ where n and R$_5$ are defined as above;

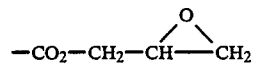

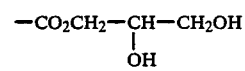

—CHO

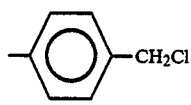

—CO$_2$(CH$_2$)$_m$NCO where m=1 to 4

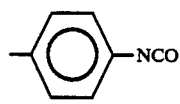

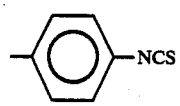

Specific examples of monomers which can be used include acrylic or methacrylic acid, acrylonitrile or methacrylonitrile, acryloyl or methacryloyl chloride, glycidyl acrylate or methacrylate, glycerol acrylate or methacrylate, allylamine, allylchloride, hydroxy-lower-alkyl acrylates (such as 2-hydroxyethylmethacrylate (HEMA) or 3-hydroxypropylmethacrylate), amino-lower-alkyl-acrylates (such as 2-aminoethylmethacrylate), and the like.

Preferred are monomers which are soluble in water or water/polar organic solvent mixtures. These can include for example, the monomers p-vinylbenzoate, styrene sulfonyl chloride, pentadienoic acid, p-ethenyl-phenylisothiocyanate, p-vinylaniline, etc.

Polymerizable mono- or polyunsaturated oligomers which may be used with or in lieu of the compounds previously described include those containing one or more olefinic groups and at least one reactive site for conjugation to a binding-pair member or spacer arm compound. Oligomers of the type which may be used include the following: (a) molecules with pendant unsaturation and reactive pendant and terminal groups; (b) molecules with pendant and terminal unsaturation and reactive pendant groups; (c) molecules with both pendant reactive and pendant unsaturated groups; (d) molecules with pendant unsaturated groups and reactive terminal groups; (e) molecules with main-chain unsaturation and reactive terminal groups; (f) molecules with main chain unsaturation and one reactive group; (g) molecules with one unsaturated terminal group and one reactive terminal group; and similar molecules.

The reactive sites on the binding-pair member or spacer-arm compound, may include, for example, functionalities such as hydroxyl, amine, carboxyl or sulfhydryl groups. These same functionalities can also be used as the reactive sites on the monomer.

Conjugation of one or more monomers to one or more binding-pair members or spacer-arm compounds may be carried out by known chemical methods. For example, the monomer and/or the binding-pair member or spacer-arm compound can be activated to produce a stable but reactive intermediate which can be subsequently conjugated. The binding-pair member can be activated, for example, by periodate oxidation of an attached carbohydrate, if the binding-pair member is glycosylated. This reaction forms aldehydes which can then condense with amino groups on a monomer such as 2-aminoethylmethacrylate to form a Schiff's base. This Schiff's base may be reduced with sodium borohydride, sodium cyanoborohydride, or a similar reducing agent to form a stable covalent linkage. Alternatively, the monomer in the form of an acid halide or anhydride may be conjugated to the binding pair member in the presence of an acid scavenger, to remove acid as it is formed during the reaction. Bifunctional or heterobifunctional (same or different functional groups) coupling reagents can be used and are well known in the art; these may be biodegradable, if desired, permitting release of the binding-pair members over an extended period of time.

In almost all cases the conditions under which the monomer/binding-pair-member conjugate is formed, i.e., time, temperature, solvents and pH, should be such as to avoid denaturation and/or degradation of the binding pair members.

The monomer may be conjugated to one or more chemical intermediary compounds which act as spacer arms, the binding-pair members also being conjugated to the spacer arm compounds. The spacer-arm provides greater accessibility of the binding-pair member's portion of the conjugate to its cognate substances in solution. The spacer-arm compound may also increase the accessibility of the monomer portion of the conjugate to other derivatized monomers and nonderivatized monomers in solution.

Chemical intermediary compounds which may be used as spacer arms include bifunctional compounds having a reactive functionality for conjugation to the monomer and a further reactive site for conjugation to the binding pair member. Reactive functionalities may include, for example, functional groups such as hydroxyl, carboxyl, amino or sulfhydryl. Examples of spacer arm compounds which may be used include, Q—(CH$_2$)$_p$—Q where p=2–10 and Q is —OH, —NH$_2$, —COOH, etc., such as ε-aminocaproic acid, 1,4-diaminobutane, hexamethylene diamine, 1,4-butanediol, p-maleimidobenzoic acid and similar compounds.

The binding pair member may also be conjugated to the monomer indirectly via an avidin-biotin bridge. For example, the binding-pair member or monomer may be biotinylated and mixed in proper proportion with cognate monomer or binding-pair-member-conjugated avidin or streptavidin.

Nonderivatized polymerizable compounds which may be used include those monomers previously discussed as suitable for conjugation to the binding-pair member. For example, monomers such as alkyl acrylates or methacrylates where the alkyl radical contains from 1–8 carbon atoms, acrylonitrile, vinylacetates and polyunsaturated monomers or oligomers previously discussed above are suitable. Also, multifunctional cross-linking compounds may be copolymerized with monomer/binding-pair-member conjugates. Such cross-linking compounds may include for example N,N'-methylenebisacrylamide or other known compounds and can be obtained, for example, from Pierce Chemical Company, Rockford, Ill.

The relative amounts of the monomer/binding-pair-member-conjugate and nonderivatized polymerizable monomer compounds employed, the composition and concentration of the unsaturated compounds; temperature; solvent, pH, and the particular initiator systems utilized allow the specific molecular engineering of a binding-pair-member-containing polymer having the properties desired. By controlled chemical synthesis it is possible to control the spacing, steric accessibility, number of binding-pair members contained in the polymer or copolymer, specific molecular weight densities, solubilities and physical structure of the polymeric conjugates, thus providing unique advantages for certain end-use applications. The binding-pair member containing polymer may be soluble or may be provided in the form of fibers, particles, beads, films, gels, tubes, filters or other shaped objects, as well as porous solids. The percentage of derivatized to nonderivatized compound in the polymer may vary from traces up to 100%, but the preferable range is between 0.001 to 100% derivatized compound and 99.99% of 0% nonderivatized compound.

Homopolymerization of the monomer/binding-pair-member conjugate with itself or copolymerization with nonderivatized polymerizable compounds can be carried out by generation of free radicals, using chemical, radiation (light, ultraviolet, gamma, or beta), and/or thermal means. Free-radical polymerizations may be conducted at moderate temperature (25° C.–45° C.), with or without agitation. A surface-active agent may or may not be present. Although the reaction may be carried out in the presence of oxygen, it is generally preferred to conduct the reaction in the absence of oxygen or in the presence of a controlled amount of oxygen. The pH range may vary widely, from pH 3 to pH 10, although it is preferable to select a pH where the binding-pair member remains the most stable, which is typically between pH 6 and pH 8 for binding-pair members such as antibodies or other proteinaceous molecules. If a surface-active agent is used, suitable compounds, such as sodium dodecyl sulfate, sodium stearate, or non-ionic materials, such as polyethyleneoxide lauryl ether may be employed.

The free radicals may be generated by redox or oxidation-reduction initiation, light or photochemical initiation, ionizing radiation initiation, or thermal initiation. An advantage of redox initiation, light or photochemical initiation and ionizing radiation is production of free radicals at reasonable rates at relatively low (25°–45° C.) temperatures.

Types of oxidation-reduction initiations which may be used include (1) peroxide in combination with a reducing agent, e.g., hydrogen peroxide with ferrous ion or benzoyl peroxide with N,N-dialkylaniline or toluidine and (2) persulfates in combination with a reducing agent such as N,N,N',N'-tetramethylethylene diamine (TEMED), sodium metabisulfite, or sodium thiosulfate. Specifically, ammonium persulfate, benzoyl peroxide, lauryl peroxide, t-butylhydroperoxide, t-butylperbenzoate, cumene hydroperoxide or mixtures thereof with reducing agents such as TEMED, sodium bisulfite, or sodium thiosulfate may be used. Sodium bisulfite alone may be used for polymerization.

Photo-initiated polymerization may also be used by employing a photo-initiator such as azodiisobutyronitrile or azodiisobutyramide. Benzoin methyl ether, riboflavin, thiazine dyes (such as methylene blue or eosin) and transition metal ions (such as ferric chloride or diazidotetraamine cobalt (III) azide) may be used in combination with ultraviolet and/or visible light irradiation of the reaction systems.

Ionizing radiation may also be employed utilizing radiation from a radioactive source or a particle accelerator.

Polymerization may be carried out in the presence of various physiological materials, such as those found in biological fluids (e.g., blood, blood serum, urine, saliva, etc.).

Monomer conjugated to a binding-pair member to form a monomer/binding-pair-member conjugate which is capable of binding to binding-pair-member cognate substances after preparation can be employed in an aqueous solution or suspension thereof for selectively binding a compound present in said solution or suspension, for purposes of analysis, isolation or purification of that compound. The binding-pair-member conjugate is incubated in the solution or suspension for an appropriate period of time to effect specific binding between the binding-pair-member conjugate and its cognate compound present in the solution or suspension. Polymerization of the conjugate is then initiated to effect separation of the polymer-bound compound from the remainder of the materials in the solution or suspension.

The monomer/binding-pair-member conjugates of this invention may also be used in immunoassays wherein it is desired to determine the presence or amount of a substance of interest (analyte binding-pair member) capable of binding to the binding-pair-member cognate in a medium suspected of containing that analyte binding-pair member. Immunoassays can take several configurations and can use a variety of reporters well-known in the art. The various possible configurations in which immunoassays may be performed are reviewed extensively in *Enzyme Immunoassay*, E. T. Maggio, Editor, CRC Press, Boca Raton, Fla., 1980 and in numerous other publications. Reporters may include radioisotopes, enzymes, coenzymes, chromophores, fluorophores, chemiluminescers, etc. and are described in a variety of publications. For example, Immunoenzymatic Techniques, *Developments in Immunology*, Vol. 18, Aurameas, S., et al., Elsevier Publications, Amsterdam, 1983.

Generally, the assay method will employ various reagents. One such reagent is a monomer/binding-pair-member conjugate which contains two portions: (1) a polymerizable monomer and (2) a second portion either directly or indirectly linked to the polymerizable monomer portion containing either the suspected analyte binding-pair member or a binding-pair-member cognate specific for a first region on the suspected analyte binding-pair member. A second reagent is a reporter/binding-pair-member conjugate capable of providing a detectable signal directly (fluorescers, chemiluminescers, dyes, enzymes, and the like) or indirectly (enzyme substrates, enzyme cofactors, enzyme inhibitors, and the like). This reporter/binding-pair-member conjugate comprises: (1) a reporter and (2) either the suspected analyte binding-pair member or a binding-pair-member cognate specific for either the first region of the analyte binding-pair member or a second region of the analyte binding-pair member.

The desired combination of reagents are combined, depending upon the specific type of immunoassay procedure employed, with the medium suspected of containing the analyte binding-pair members under conditions that favor complex formation. Such factors as salt concentration and type, buffer strength, temperature, pH, and the like may be used to stimulate or retard complex formation.

Once the complex is formed, polymerization may be initiated by any of the procedures described above. The polymerization may include nonderivatized polymerizable monomers and/or nonderivatized multifunctional cross-linking compounds. It is contemplated that in addition to the nonderivatized polymerizable monomer and/or nonderivatized multifunctional cross-linking compounds, polymerizable monomers and/or multifunctional cross-linking compounds may be present that are bound to an assay container wall thus serving as bridges to link the polymer or copolymer to the assay container.

After the polymerization of copolymerization is complete, the presence or amount of the suspected analyte binding-pair member is determined. The amount of the polymer-bound or unbound reporter may be determined by an appropriate means corresponding to the type of reporter employed in the assay and the presence and quantity of analyte binding-pair member established.

Specifically, in a competitive immuunoassay, for example, a sample suspected of containing an analyte binding-pair member is incubated with a monomer/analyte conjugate and a reporter/receptor conjugate. The receptor is typically an antibody to the analyte. If the analyte is itself an antibody, the receptor can be a second antibody to the first antibody, or it can be the antigen of the first antibody. Analyte present in sample and monomer/analyte conjugate compete for a limited amount of reporter/receptor. Polymerization-induced separation of free from specifically bound reporter/receptor enables the detection and measurement of analyte initially present in the sample. The above assay can also be performed using a monomer/receptor conjugate and a reporter/labelled analyte.

In another configuration monomer/binding pair member conjugates of this invention can be utilized in sandwich immunoassays. This configuration is appropriate for analytes which have more than one antigenic determinant. In this case, sample suspected of containing analyte binding-pair member is incubated with a monomer/receptor conjugate and a reporter/receptor conjugate. After a period of incubation sufficient to allow specific binding to occur, polymerization is carried out and the presence or amount of reporter/receptor specifically bound to the resultant polymer is determined. The polymer particles can be washed, if desired, to remove any non-specifically bound reporter/receptor.

Discrimination of reporter/receptor associated with the resultant polymer from free reporter/receptor can be accomplished by any of a number of methods, including flow microfluorimetry, filtration, and centrifugation.

Polymers or copolymers integrally containing suitable binding-pair members such as antigens, haptens, and the like may find use in immunization regimes when employed in a physiologically acceptable carrier as a vaccine. A host may be immunized against organisms or particles presenting binding pair members, such as antigens, haptens, and the like. The manner of administration may be varied widely in methods well-known in the art, which include but are not limited to oral, parenteral, (by intravenous or subintaneous injection), or the like. Dosage levels, desired adjuvant effects, number of administrations, frequency of boosters and the like will vary depending upon the route of administration, type and size of host, and similar considerations.

The following examples are offered by way of illustration and not by way of limitation.

EXPERIMENTAL

In the following examples, a variety of monomers are conjugated to antibody by several synthetic routes and the resultant conjugates are employed in a variety of immunoassay configurations. Example I demonstrates covalent conjugation of the active ester of an acrylic acid monomer to a monoclonal antibody to form a monomer/antibody conjugate which is immunoreactive and polymerizable. Example II demonstrates conjugation of the monomer styrene sulfonyl chloride to a monoclonal antibody and its use in a sandwich immunoassay for human IgG. Example III describes conjugation of the monomer pentadienoic acid to an antibody and its use in an immunoassay for human IgG. Example IV describes conjugation of the monomer p-vinylaniline to a monoclonal antibody to form an immunoreactive and polymerizable conjugate. Example V describes conjugation of the monomer isothiocyanatophenylacetylene to a monoclonal antibody and its use in an immunoassay for human IgG. Example VI describes conjugation of the monomer vinyl benzoate to a monoclonal antibody via an avidin-biotin bridge and its use in a sandwich immunoassay. Example VII describes a competitive immunoassay for digoxin.

EXAMPLE I

Synthesis and Polymerization of an Immunoreactive Acrylic Acid/Antibody Conjugate A. Synthesis Of An Activated Acid Monomer For Conjugation To Antibody A mixture containing N-hydroxysuccinimide (NHS, 4.6 gms, 40 mmol), and acryloyl chloride (18 ml, 222 mmol) was refluxed with vigorous stirring for 3 hours in an anhydrous atmosphere, and the reaction mixture, a homogeneous solution, was evaporated to a syrup. Distilled water (50 ml) was added to the syrup and the mixture was stirred for 30 minutes at 4° C. Upon addition of chloroform (50 ml) the mixture was separated into layers and the organic layer was extracted successively with water (50 ml each time, five times usually) until the pH of the water layer was approximately 5. The aqueous solutions so obtained were combined and extracted once with chloroform (50 ml). This chloroform solution and the chloroform solution from above were combined, dried over sodium sulfate, and evaporated to a syrup. Crystals obtained by storing the syrup overnight at −20° C. were triturated with diethylether and harvested by filtration. Recrystallization from absolute ethanol yielded 2 gm of the desired product. This compound was analyzed by mass spectrometry, infrared spectroscopy, NMR, liquid chromatography, and melting point, and proved to be the N-hydroxysuccinimide ester of acrylic acid.

B. Preparation And Characterization Of A Monomer/Antibody Conjugate

A mouse monoclonal antibody to the kappa light chain of human IgG was prepared by standard methods. This antibody, designated 2Hl, was purified by ammonium sulfate precipitation and affinity chromatography on protein A. The N-hydroxysuccinimide ester of acrylic acid (NSA) was reacted with mouse monoclonal antibody (MAb) 2Hl as follows: 2.2 mg MAb in 0.29M sodium carbonate buffer, pH 9.3, was added to 20 μg of NSA in a total volume of 0.5 ml. The reaction mixture was incubated at 37° C. for one hour with constant stirring. 100 μl of this solution was then taken for an analysis by reversed phase high performance liquid chromatography (RP-HPLC), which revealed the amount of free acrylic acid arising from hydrolysis of NSA and remaining NSA in the reaction mix. This analysis indicated that a net of 89 nmoles of monomer was attached to 14.5 nmoles of MAb for a ratio of 6.2 monomer molecules per MAb.

To remove residual NSA and its hydrolysis products and for further characterization of the derivatized antibody, 200 µl of the reaction mixture was chromatographed on a column of Sephadex G-25 (beads of dextran cross-linked with epichlorohydrin from Pharmacia Fine Chemicals AB, Uppsala, Sweden) equilibrated in the same carbonate buffer containing bovine serum albumin, 0.1 mg/ml.

To show that the purified monomer/antibody conjugate was still active, it was tested in an enzyme-linked immunosorbent assay (ELISA), and the results indicated no loss of antigen binding capacity. For this purpose human IgG, which contains kappa light chains, that was reactive with antibody 2H1 was adsorbed to the surfaces of wells in a microELISA plate (96 well). The wells were washed, residual nonspecific adsorbing sites on the plastic surface were blocked with bovine serum albumin, and then the wells were incubated with serial dilutions of the antibodies (control unconjugated antibody, or monomer/antibody conjugate). The plate was again washed, incubated with goat anti-mouse immunoglobulin conjugated to horseradish peroxidase (Tago, Inc., Burlingame, Calif. 94010), washed, and incubated with the substrates for horseradish peroxidase, hydrogen peroxide and o-phenylenediamine (OPD). Dilute aqueous sulfuric acid was added to stop the reaction, the plates were assayed on a microELISA reader, and the optical densities of the contents of the wells determined. On a molar basis the monomer/antibody conjugate demonstrated comparable immunoreactivity to the unconjugated control antibody.

A sample of the monomer/antibody conjugate was then analyzed by isoelectric focusing, which procedure separates the polypeptide subunits of proteins according to their isoelectric points (pH at which they have no net positive or negative charge). For this purpose, heavy and light chains of the monomer/antibody conjugates were first dissociated in the presence of 3% (w/v) sodium dodecyl sulfate (SDS) and 5% (v/v) 2-mercaptoethanol, and separated on the basis of molecular weight by electrophoresis in an SDS/polyacrylamide slab gel. The separated heavy and light chains were cut out from the gel and analyzed further by isoelectric focusing in a polyacrylamide slab gel, according to their isoelectric point. Staining of the focusing gel with Coomassie Brilliant Blue R250 provided a characteristic pattern band for each sample. Since both the heavy and light chains of antibodies are glycoproteins which contain intrinsic variations in their sialic acid content, each heavy and light chain can be separated by charge into a characteristic family of bands, the different bands comprising polypeptides differing in their amounts of sialic acid. As the reaction of the activated acrylic acid occurred primarily with amino functional groups on protein lysine residues, the conjugation of monomers to monoclonal antibody would be expected to neutralize one positive charge on the protein subunit for each molecule of acrylic acid attached. This in turn would be expected to change the isoelectric point of the derivatized protein.

The results of isoelectric focusing analysis indicated that each heavy chain was modified by the covalent attachment of approximately three acrylic acid monomers. Analysis also indicated that the electrophoretic pattern of monomer-derivatized light chains was so close to the nonderivatized polypeptide pattern that essentially minimal conjugation of the monomer to light chain had occurred. On this basis, it was estimated that 6 moles of acrylic acid were conjugated to each mole of antibody (3 per heavy chain×2 heavy chains per antibody), which was in agreement with the analysis by RP-HPLC.

C. Demonstration Of Incorporation Of Monomer-/Antibody Conjugate Into Polymer

In order to provide a means of identifying and monitoring the presence of antibody molecules in polymers, the monomer/antibody (MAb/M) conjugate was covalently tagged with a fluorescent compound. For this purpose, 88 µg (8.8 µl of a 10 mg/ml solution in DMSO) of fluorescein isothiocyanate (FITC), isomer II, was added to 3.6 mg of MAb/M in 1.2 mls of 0.29M carbonate buffer, pH 9.3. The mixture was stirred for one hour at 37° C. and chromatographed on a column of Sephadex G-25 in phosphate buffered saline (PBS) to which bovine serum albumin (0.01 mg/ml) had been added. This separated the fluorescein-tagged monoclonal antibody/monomer conjugate from any free FITC that remained in solution.

The fluorescein-tagged conjugates were then copolymerized with 2-hydroxyethylmethacrylate (HEMA) to form insoluble polymer particles. This and appropriate controls were analyzed by flow microfluorimetry. For analysis by flow microfluorimetry, polymerization was allowed to proceed for 10 minutes. The suspension of polymer particles was then diluted 100 fold and introduced into a Becton-Dickinson FACS IV, equipped with an Argon ion laser light source. In this procedure, the suspended particles are carried single file in a laminar stream of buffer. Interrogation of the particle stream with the laser beam generates a light scatter signal each time a particle enters the laser pathway. The extent of the light scatter is a reflection of particle size and shape. Further, measurement of light scatter can also be used to electronically trigger a simultaneous measure of fluorescence emitted from the particles. In this way fluorescence specifically associated with polymer particles can be selectively measured.

Light scatter analysis of polymer particles formed with HEMA alone, polymer particles formed from HEMA polymerized in the presence of fluorescein-tagged bystander antibody, and polymer particles formed by copolymerization of HEMA with monomer-conjugated, fluorescein-tagged MAb, shows that the particle-size distribution was substantially the same for all three samples. The fluorescence intensity of polymer particles formed from HEMA alone and polymer particles formed from HEMA polymerized in the presence of bystander antibody indicate fluorescence intensity was substantially the same for both samples. Since the intensity was the same regardless of whether or not fluorescein-tagged bystander antibody was present, the weak fluorescence signal of both samples was assumed to be due to autofluorescence of the HEMA polymer itself and indicated that there was minimal nonspecific entrapment of the bystander antibody in the polymer. The fluorescence intensity of copolymer particles formed by copolymerization of monomerderivatized, fluorescein-tagged monoclonal antibody and HEMA was shifted over 28 channels relative to the control. The fluorescence intensity scale is logarithmic and a shift of 28 channels corresponds to a 3-fold increase in fluorescence intensity. This dramatic increase in the fluorescence intensity provided conclusive evidence that the monomer-derivatized, fluorescein-tagged monoclonal antibody was integrally incorporated into the polymer particles.

EXAMPLE II

Synthesis and Use in an Immunoassay of a p-Styrene Sulfonyl Chloride/Antibody Conjugate A. Synthesis of p-Styrene Sulfonyl Chloride For Conjugation To Antibody Sodium p-styrene sulfonate (20 g) was slowly added in small portions to thionyl chloride (50 ml) and dimethyl formamide (50 ml) in an ice bath. The mixture was stirred for three hours at room temperature, poured into 300 ml of cold water, and extracted twice with benzene. After washing the benzene extract twice with water, anhydrous magnesium sulfate was added and then removed by filtration. The dry benzene extract was concentrated on a rotary evaporator and the residual benzene removed under high vacuum.

The product was analyzed by thin layer chromatography, nuclear magnetic resonance spectroscopy, and mass spectrometry, and was shown to be p-styrenesulfonyl chloride (SSC).

B. Preparation And Characterization Of A Monomer/Antibody Conjugate

Murine monoclonal antibody 2HI was conjugated to SSC as follows: to 2.3 mg of purified 2HI in 0.4 ml of 0.29M carbonate buffer, pH 9.3 was added 98 μg of SSC in 20 μl of tetrahydrofuran. The reaction mixture was incubated at 37° C. for one hour, then applied to a column of Sephadex G-25 equilibrated with phosphate-buffered saline (PBS), and eluted with PBS.

The absorbance of the conjugate was determined at 260 nm (due to SSC) and at 280 nm (due to protein) and the number of monomers per antibody molecule calculated, using $2 \times 10^4 M^{-1} cm^{-1}$ for the extinction coefficient of SSC. Based on these calculations, there were approximately eight monomers per antibody.

C. Assay By Flow Microfluorimetry

A sandwich immunoassay for human IgG was performed. For this purpose a human myeloma protein (IgG/kappa) was used as the antigen. A monoclonal antibody, designated 3F6, reactive with the gamma heavy chain of IgG, was labelled with fluorescein isothiocyanate, as described above (Example I.C.) to yield $Ab_F$.

MAb/M (30 μg/ml final), AbF (10 μg/ml final), and HEMA (1% (w/v) final) were incubated with varying concentrations of antigen in a total volume of 100 μl PBS/BSA. After incubation for 20 minutes at 37° C., polymerization was initiated by the addition of 25 μl of 0.24M TEMED and 25 μl of 30 mM ammonium persulfate. Polymerization was allowed to continue for 20 minutes, at which time a 50 μl aliquot was withdrawn and diluted into 2 ml PBS for analysis by flow microfluorimetry. The peak channel numbers and the corresponding linear fluorescence units at different antigen levels are given in Table I.

TABLE I

Reactivity of Styrene Sulfonyl Conjugated-2HI in a Polymerization Induced Separation Immunoassay for Human IgG

| (Human IgG) g/ml | Peak Channel | Linear Fluorescence Units |
|---|---|---|
| 2 | 112 | 96.2 |
| 1 | 92 | 42.6 |
| 0.5 | 66 | 14.7 |
| 0.25 | 52 | 8.3 |
| 0.125 | 37 | 4.5 |

TABLE I-continued

Reactivity of Styrene Sulfonyl Conjugated-2HI in a Polymerization Induced Separation Immunoassay for Human IgG

| (Human IgG) g/ml | Peak Channel | Linear Fluorescence Units |
|---|---|---|
| 0.0625 | 36 | 4.3 |
| 0.03125 | 34 | 4.0 |
| 0.0156 | 32 | 3.7 |
| 0 | 29 | 3.3 |

*Assayed by flow microfluorimetry.

EXAMPLE III

Synthesis and Use in an Immunoassay of a Pentadienoic Acid/Antibody Conjugate

A. Synthesis Of The N-hydroxysuccinimide (NHS) Ester Of 2,4-Pentadienoic Acid (PDA)

To 1 g (10.3 mmoles) of PDA in 40 ml of tetrahydrofuran was added 1.18 g of NHS and 2.12 g of dicyclohexyl carbodiimide. The reactants were stirred overnight at room temperature and then filtered through a sintered-glass vacuum filter. To 25 ml of the resulting filtrate was added 75 ml of heptane. The turbid solution was again filtered, the filtrate cooled at −25° C., and the resulting crystals collected by filtration. The crystals were analyzed by melting point (82°–83° C.), thin layer chromatography, and nuclear magnetic resonance spectroscopy and proved to be the NHS ester of PDA (NSP).

B. Preparation And Characterization Of A Monomer/Antibody Conjugate

The murine monoclonal antibody designated 2HI was conjugated with NSP to yield a pentadieneamide/antibody conjugate as follows: To 2.9 mg of purified 2HI MAb in 0.51 ml of 0.29M carbonate buffer, pH 9.3 was added 30 μg NSP in 6 μl of tetrahydrofuran. After one hour incubation at 37° C., 50 μl of the solution was taken for analysis by RP-HPLC, which revealed the amounts of free PDA arising from hydrolysis and remaining NSP in the reaction mix. This analysis indicated that approximately 5.4 monomers were conjugated per antibody.

The conjugate was further purified by chromatography on a column of Sephadex G-25 equilibrated with phosphate-buffered saline (PBS) to remove residual NSP and its hydrolysis products. A sample of the monomer/antibody conjugate was then analyzed by isoelectric focusing as described in sample I(B) above. On this basis it was estimated that 5.7 moles of pentadienoic acid were conjugated to each mole of antibody, which was in agreement with analysis by RP-HPLC.

C. Assay by Flow Microfluorimetry

A sandwich immunoassay for human IgG, similar to that described in Example IIC and using the same antigen and the same 3F6-FITC conjugate, was performed.

Mab/M (30 μ/ml final concentration), $Ab_F$(10 μg/ml final concentration), and HEMA (1% (w/v) final concentration) were incubated with varying concentrations of antigen in a total volume of 80 μg PBS. After incubation for 20 minutes at 37° C., polymerization was initiated by the addition of 10 μl of 0.4M TEMED and 10 μl of 0.05M ammonium persulfate. After incubation for ten minutes, a 50 μl aliquot was withdrawn for analysis by flow microfluorimetry. A standard curve was obtained.

EXAMPLE IV

Synthesis of an Immunoreactive p-Vinylaniline/Antibody Conjugate

A. General

In this example the monomer p-vinylaniline (PVA) was conjugated to antibody through the carbohydrate moieties on the latter. This was accomplished by first oxidizing the carbohydrate cisdiols to aldehydes, condensing the latter with an amine group on the monomer to form an imine, and then stabilizing the resultant linkage by reduction of the imine with sodium cyanoborohydride.

B. Preparation And Characterization Of A Monomer/Antibody Conjugate

PVA was reacted with MAb 2HI as follows: Antibody 2HI (6.6 mg/ml) was dialyzed against two changes of deionized water (4 liters) at 4° C. The antibody concentration was adjusted to 4.0 mg/ml. 0.4 ml of 0.1M NaIO4 was added to 8.5 mg of antibody. After stirring at room temperature for 20 minutes, the reaction mix was purified by gel filtration on Sephadex G-25 equilibrated with PBS, pH 7.0. The protein-containing fractions were pooled and 7.2 $\mu$l of 5M PVA was added to a 2.5 mg aliquot that had been sparged with dry prepurified nitrogen gas. The tube was covered and shaken for 45 minutes at room temperature, then 4.5 mg of sodium cyanoborohydride was added. The reaction mix was incubated at 4° C. for 3 hours and then dialyzed against PBS, pH 7.4 for 36 hours.

C. Demonstration Of Incorporation Of Monomer/Antibody Conjugate Into Polymer

For this purpose, a human IgG myeloma protein having kappa light chains was used as the source of antigen. Antigen was diluted to the desired concentration in buffer and reacted with the PVA/MAb-2HI conjugate (MAb/M, prepared above) and with a fluorsceinated MAb (3F6) to the gamma heavy chain of IgG (Ab$_F$). After sufficient time had elapsed to allow sandwich formation to occur, the reaction mixture was polymerized and the amount of fluorescence associated with the resultant particles was determined after filtration on the Screen Machine (Pandex Laboratories, Mundelein, IL).

The Screen Machine utilizes 96-well microtiter plates in which the bottoms of the wells have been replaced with porous cellulose acetate filters (0.22$\mu$ average pore size). When suction is applied to the plates, liquid is pulled through while particulates are retained on the filters. The filters can be washed a variable number of times and the amount of fluorescence trapped thereon determined at any of several wavelengths.

For purposes of this experiment the filters were prewashed with 1% BSA in PBS. MAb/M (final concentration of 30 $\mu$g/ml) and AbF (10 $\mu$g/ml) were incubated with antigen (0 or 1 $\mu$g/ml final) in a total volume of 100 $\mu$l PBS/BSA for 20 minutes at 37° C. Polymerization was initiated by the addition of 25 $\mu$l of 0.24M TEMED and 25 $\mu$l of 30 mM ammonium persulfate and allowed to continue for 20 minutes at 37° C. A 50-$\mu$l aliquot was withdrawn and diluted with an equal volume of PBS containing 0.05% (w/v) Tween 20 for analysis. Under these conditions the signal: background ratio was found to be approximately 5.

EXAMPLE V

Synthesis Of An Immunoreactive Isothiocyanato-phenylacetylene Antibody Conjugate A. Preparation and Characterization Of A Monomer/Antibody Conjugate Isothiocyanato-phenylacetylene (IPA) was conjugated to monoclonal antibody 2HI, which is reactive with the kappa chains of human immunoglobulin, as follows: IPA was dissolved in THF at 10 mg/ml and 17.2 microliters of the solution was added to a solution of 3 mg of 2HI in 0159 ml of 0.29M carbonate buffer pH 9.3. After stirring for one hour at 37° C. the reaction mix was added to a column of Sephadex G-25 which had been pre-equilibrated with PBS. The monomer/antibody conjugate was eluted with PBS.

Isoelectric focusing indicated that this monomer/antibody conjugate contained between 5 and 6 monomers per antibody.

B. Assay By Flow Microfluorimetry

An assay for Human IgG was performed as described in section II C above using the isothiocyanato-phenylacetylene/antibody (2HI) conjugate. A 50-$\mu$l aliquot of the polymerization reaction mix was diluted into 2 mls PBS and assayed by flow microfluorimetry. The peak channel numbers and the corresponding linear fluorescence calls for different antigen levels are given in Table 2.

TABLE II

| Reactivity of Isothiocyanato-phenylacetylene Conjugated 2HI In Polymerization Induced Separation Immunoassay for IgG | | |
|---|---|---|
| (Human IgG) g/ml | Peak Channel | Linear Fluorescence Units |
| 2 | 91 | 40.9 |
| 1 | 63 | 13.0 |
| 0.5 | 48 | 7.1 |
| 0.25 | 37 | 4.5 |
| 0.125 | 33 | 3.8 |
| 0.0625 | 31 | 3.5 |
| 0.03125 | 28 | 3.1 |
| 0 | 22 | 2.5 |

*Assayed by flow microfluorimetry.

EXAMPLE VI

Synthesis Of A Monomer/Antibody Conjugate In Which The Monomer And The Antibody Are Joined By An Avidin-Biotin Bridge A. General In this example, monomer (vinyl benzoate) was conjugated to antibody (2HI) indirectly via an avidinbiotin bridge. Biotinylated antibody and monomer-conjugated avidin were mixed immediately before use and added to the assay as a preformed complex.

B. Preparation And Characterization Of A Monomer/Antibody Conjugate

1. Preparation Of A Monomer/Avidin Conjugate

To 5 mg of avidin dissolved in 0.5 ml of 0.29M carbonate buffer, pH 9.3 was added 558 mg of N-succinimidyl(4-vinylbenzoate) (NSB) in 55.8 $\mu$l of tetrahydrofuran (THF). The reaction mixture was stirred for one hour at 37° C., and a 50-microliter aliquot was then taken for analysis by RP-HPLC. Results of this analysis indicated that 20.2 monomers were conjugated per avidin molecule. To remove residual NSB and its hydrolysis products the remainder of the reaction mixture was chromatographed on a column of Sephadex G-25 equilibrated with PBS.

2. Preparation Of A Biotin/Antibody Conjugate

The N-hydroxysuccinimide ester of biotin (NBI) was reacted with monoclonal antibody (MAb) 2H1 as follows: to 2.0 mg MAb in 0.36 ml of 0.29M carbonate buffer, pH 9.3 was added 13.6 μg of NBI in 6.8 μl of THF. After stirring for one hour at 37° C., a 50-μl aliquot was taken for analysis by RP-HPLC. From this analysis it was determined that each conjugate contained an average of 3.9 biotin molecules per antibody molecule. This conjugate was then purified on a column of Sephadex G-25 equilibrated with PBS.

3. Formation Of A Monomer/Avidin-Biotin/Antibody Complex

Monomer/avidin conjugate (1 μg/ml) was added slowly with stirring to biotin/antibody conjugate (10 μg/ml) form a complex in which the monomer was attached to the antibody via an avidin-biotin bridge. The complex was formed immediately before use.

C. Assay By Flow Microfluorimetry

An assay for human IgG was performed as described in Example II.C above. A 50-μl aliquot of the polymerized reaction mixture was diluted into 2 ml of PBS and assayed by flow microfluorimetry. A standard curve for human IgG was obtained.

EXAMPLE VII

Competitive Immunoassay For Digoxin

A. General

In this example, a competitive assay for digoxin is carried out using a fluorescently labelled digoxin analog and a monomer conjugate antibody to digoxin.

B. Synthesis Of Reagents

1. Digoxigenin-3-O-Hemisuccinate

Digoxigenin-3-O-hemisuccinate was prepared, purified by thin layer chromatography (silica gel, ethyl acetate/methanol, 95:5), and shown to melt at the expected temperature.

2. Purification Of R-Phycoerythrin (R-PE).

R-PE was purified from *Porphyra yezoensis* red algae by the procedure of Ledbetter et al. (Lymphocyte Surface Antigens, Perspective in Immunogenetics and Histocompatibility, Vol. 6, p 119–129, 1984).

3. Digoxigen/R-PE Conjugation

The mixed acid anhydride method of Comoglio and Celada (J. Imnunol. Meth. 10: 161–170, 1976) was used to conjugate digoxigenin-3-O-hemisuccinate to R-PE. Digoxigenin-3-O-hemisuccinate (7 mg) was dissolved in 284 μl of dry dioxane. To that solution, 9 μl of tributylamine was added and the solution was cooled to about 10°-12° C. Seven microliters of isobutylchloroformate was then added and the reaction mixture stirred for 20 minutes while maintaining the temperature at about 10°-12° C. Ten microliters of the above mixed anhydride solution was added to 1 ml of a cooled solution of R-PE dissolved in water to a concentration of 1 mg/ml. The reaction mixture was stirred overnight at 4° C. and then applied to a Sephadex G-25 column (1×35 cm). The column was eluted with PBS containing 0.1% NaN3. The R-PE-containing fractions were pooled and stored at 4° C.

4. Preparation Of An IgG Fraction Of Digoxin Antiserum

An IgG fraction of a rabbit anti-digoxin antiserum was obtained by DEAE Affi-Gel Blue chromatography. To 5 ml of DEAE Affi-Gel Blue equilibrated with 0.02M $K_2HPO_4$, pH 8.0, was applied 1 ml of antiserum which had been dialyzed against 0.02N $K_2HPO_4$, pH 8.0. The column was eluted with two-bed volumes of 0.02M $K_2HPO_4$, pH 8.0. The protein containing fractions were pooled and concentrated to about 2 mg IgG/ml.

5. Monomer/Antibody Conjugation

The monomer vinyl benzoate was conjugated to the aantibody prepared above as described in the copending patent application U.S. Ser. No. 668,247 at a molar ratio of 40:1.

C. Assay

The assay was performed as follows. A fifty-microliter sample of digoxin standard, 50 μl of MAb/M and 50 μl of 6% HEMA in 1% BSA-PBS were incubated for 60 minutes at 37° C. Then 50 μl of digoxigenin-3-O-hemisuccinate/R-PE conjugate diluted 2,000 fold with PBS/1% BSA was added and the mixture incubated for another 60 minutes at 37° C. Polymerization was initiated by the addition of 50 μl of TEMED (0.24M) and 50 μl of ammonium persulfate (0.03M). Fifty microliters of the assay mixture was diluted with an equal volume of PBS/BSA and analyzed on the Screen Machine. A standard curve was obtained. When antigen was added in serum, a similar standard curve was achieved.

All publications, patents, and patent applications listed in this specification are indicative of the level of skill of those skills in the art to which this invention pertains. Each individual publication, patent, and patent application is herein individually incorporated by reference to the same extent as if each item had been individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for the de novo synthesis of a polymer integrally containing a binding-pair member comprising:
    forming a monomer/binding-pair-member conjugate containing one or more binding-pair members joined to one or more monomers; and
    initiating polymerization of the monomer/binding-pair-member conjugate to form said polymer.

2. A method according to claim 1, wherein said binding-pair member is indirectly linked to said monomer by a spacer arm.

3. A method according to claim 1, wherein said binding-pair member is indirectly linked to said monomer by an avidin- or streptavidin-biotin bridge.

4. A method according to any of claims 1, 2, or 3, wherein said binding-pair member linked to said monomer to form said conjugate is selected from receptors and their ligands.

5. A method according to any of claims 1, 2, or 3, wherein said binding-pair member linked to said monomer to form said conjugate is selected from antibodies and their antigens.

6. A method for the de novo synthesis of a polymer integrally containing a binding-pair-member comprising:
    forming a monomer/binding-pair-member conjugate containing one or more binding-pair members joined to one or more monomers; and
    initiating polymerization of the monomer/binding-pair--member conjugate in the presence of a nonderivatized polymerizable monomer or a nonderivatized polymerizable multifunctional cross-linking compound or a mixture thereof so as to form a copolymer.

7. A method according to claim 6, wherein said binding-pair member is indirectly linked to said monomer by a spacer arm.

8. A method according to claim 6, wherein said binding-pair member is indirectly linked to said monomer by an avidin- or a streptavidin-biotin bridge.

9. A method according to any of claims 6, 7, or 8, wherein said binding-pair member linked to said monomer to form said conjugate is selected from antibodies and their antigens.

10. A method according to any of claims 6, 7, or 8, wherein said binding-pair member linked to said monomer to form said conjugate is selected from receptors and their ligands.

11. A monomer/binding-pair-member conjugate containing one or more polymerizable monomers linked to one or more binding-pair members wherein said conjugate is used in the de novo synthesis of a polymer integrally containing said bindinbg-pair members.

12. A monomer/binding-pair-member conjugate used in the de novo synthesis of a polymer or a copolymer formed with a nonderivatized monomers, a multifunctional cross-linking compound, or a mixture thereof, comprising:
a monomer containing at least one reactive site capable of direct linking with a binding-pair member or indirect linking via a spacer arm with a binding-pair member covalently linked to a binding-pair member containing a reactive site capable of direct direct linking with said monomer or indirect linking via said spacer arm with said monomer, respectively.

13. A conjugate according to claims 11 or 12, wherein the binding-pair member is selected from receptors and their ligands.

14. A conjugate according to claims 11 or 12, wherein the binding-pair member is selected from antibodies and their antigens.

15. A conjugate according to claims 11 or 12, wherein said monomer is indirectly linked by an avidin- or streptavidin-biotin bridge to said binding-pair member.

16. A conjugate according to claims 11 or 12, wherein said monomer is of the formula:

$$R_1\!\!\diagdown\!\!_{C=C}\!\!\diagup\!\!R_3$$
$$R_2\!\!\diagup\quad\diagdown\!\!R_4$$

where $R_1$ and $R_3$ equal H or methyl; $R_2$ equals H, methyl, or ethylene; and $R_4$ equals:
—COCl
—CN
—OH
—COOH
—COOR$_5$ where R$_5$=an alkyl group having from 1-6 carbon atoms;

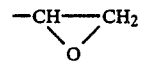

—CO$_2$(C$_n$H$_{2n}$)OH where n=2 to 4
—NH$_2$

—NHR$_5$ where R$_5$ is defined as above;
—NCO
—CONH$_2$
—CONHR$_5$ where R$_5$ is defined as above;
—CONHCH$_2$OH
—CH$_2$NH$_2$
—CH$_2$Cl
—CO$_2$(C$_n$H$_{2n}$)NH$_2$ where n is defined as above;
—CO$_2$(C$_n$H$_{2n}$)NHR$_5$ where n and R$_5$ are defined as above;

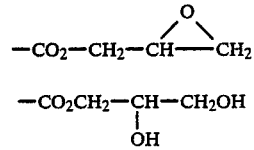

—CHO

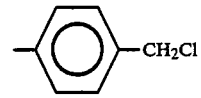

—CO$_2$(CH$_2$)$_m$NCO where m=1 to 4

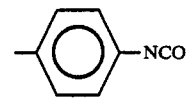

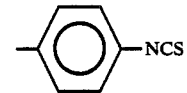

17. A polymer integrally containing binding-pair members synthesized from polymerizable monomer/-binding-pair-member conjugates.

18. A polymer or copolymer integrally containing binding-pair members, wherein said polymer or copolymer is synthesized from (a) polymerizable monomer/-binding-pair-member conjugates or (b) said conjugate and polymerizable nonderivatized monomers or multifunctional cross-linking compounds, respectively.

19. A polymer according to claims 17 or 18, wherein said conjugates each contain one or more binding-pair members that are directly linked to one or more monomers or are indirectly linked to one or more monomers via a spacer arm and said binding-pair members are selected from antibodies and their antigens.

20. A polymer according to claims 17 or 18, wherein said conjugates each contain one or more binding-pair members that are directly linked to one or more monomers or are indirectly linked to one or more monomers via a spacer arm and said binding-pair members are selected from receptors and their ligands.

21. A polymer according to claims 17 or 18, wherein one or more monomers are indirectly linked to one or more binding-pair members by avidin- or streptavidin-biotin bridges.

22. An assay method for determining the presence of an analyte binding-pair member in a medium suspected of containing said analyte binding-pair member, employing as reagents: (1) a monomer/binding-pair-member conjugate comprising (i) a polymerizable monomer and (ii) either said analyte binding-pair member or a binding-pair-member cognate specific for a first region on said analyte binding-pair member; and (2) a reporter/binding-pair-member conjugate capable of providing directly or indirectly a detectable signal comprising (i) a reporter and (ii) either said analyte binding-pair member or a binding-pair-member cognate specific for either said first region of said analyte binding-pair member or a second region of said analyte-binding pair member;

said method comprising:

combining said reagents with said medium suspected of containing said analyte binding-pair member under conditions favoring complex formation whereby complex formation occurs between (1) and (2);

polymerizing said monomer/binding pair member complex with or without nonderivatized polymerizable monomers, or nonderivatized polymerizable multifunctional cross-linking compounds, or a mixture thereof; and determining the distribution of said reporter between reporter bound and unbound to polymer.

23. An assay method according to claim 22, wherein said monomer/binding-pair-member conjugate contains either an antibody or antigen as said analyte binding-pair member or said binding-pair-member cognate and said reporter/binding-pair-member conjugate contains either antigen or antibody as said analyte binding-pair member or said binding-pair-member cognate.

24. An assay method according to claim 22, wherein said monomer/binding-pair-member conjugate contains analyte or receptor bound to said monomer and said reporter/binding-pair-member conjugate contains analyte or receptor bound to said reporter.

25. An assay method according to claim 22, wherein said monomer/binding-pair-member conjugate contains a receptor bound to said monomer, wherein said receptor is specific for a first region on said analyte binding-pair member and said reporter/binding-pair-member conjugate contains a receptor bound to said reporter, wherein said receptor is specific for a second region on said analyte binding-pair member.

26. An assay method according to any of claims 22, 23, 24, or 25, wherein said polymerizing occurs with nonderivatized polymerizable monomers or nonderivatized polymerizable multifunctional cross-linking compounds that are linked to the wall of an assay container.

27. An assay method according to any of claims 22, 23, 24, or 25, wherein said analyte binding-pair member or binding-pair-member cognate is bound to said polymerizable monomer by an avidin- or strepavidin-biotin bridge.

28. A kit for detecting the presence of an analyte binding-pair member in a medium suspected of containing said analyte binding-pair member, said kit comprising: (1) a monomer/binding-pair-member conjugate comprising (i) a polymerizable monomer and (ii) either said analyte binding-pair member or a binding-pair-member-cognate specific for a first region on said analyte binding pair member; and (2) a reporter/binding-pair-member conjugate capable of providing directly or indirectly a detectable signal comprising of; (i) a reporter and (ii) either said analyte binding-pair member or a binding-pair-member cognate specific for either said first region of said analyte binding-pair member or a second region of said analyte binding-pair member.

29. A kit according to claim 28, wherein said reporter is a fluorescer or enzyme.

30. A method of immunizing a host to protect said host from organisms or particles presenting binding-pair members, which comprises:

administering to said host an amount effective to induce immunization of a polymer or copolymer integrally containing binding-pair members to elicit an immunogenic response in a physiologically acceptable carrier.

31. A method according to claim 30, wherein said binding pair-members are haptens or antigens.

* * * * *